(12) United States Patent
Reinhardt et al.

(10) Patent No.: US 7,727,774 B2
(45) Date of Patent: Jun. 1, 2010

(54) METHOD AND APPARATUS FOR AUTOMATED COVERSLIPPING

(75) Inventors: Kurt Reinhardt, Tucson, AZ (US); Anthony Ford, Tucson, AZ (US); Mirek Holubec, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 350 days.

(21) Appl. No.: 11/838,104

(22) Filed: Aug. 13, 2007

(65) Prior Publication Data

US 2008/0029218 A1 Feb. 7, 2008

Related U.S. Application Data

(62) Division of application No. 10/424,335, filed on Apr. 25, 2003, now Pat. No. 7,271,006.

(60) Provisional application No. 60/375,925, filed on Apr. 26, 2002.

(51) Int. Cl.
*G01N 1/10* (2006.01)
(52) U.S. Cl. .......................... 436/180; 422/63; 422/64; 422/65; 422/67; 156/344; 436/46
(58) Field of Classification Search ................. 156/344; 422/63–67; 436/180, 46
See application file for complete search history.

(56) References Cited

U.S. PATENT DOCUMENTS

| | | |
|---|---|---|
| 3,930,928 A | 1/1976 | Tapert |
| 4,428,793 A | 1/1984 | Sato et al. |
| 4,455,188 A | 6/1984 | Stormby |
| 5,193,796 A | 3/1993 | Nagai et al. |
| 5,580,414 A | 12/1996 | Ljungmann |
| 5,989,386 A | 11/1999 | Elliott |
| 6,382,693 B1 | 5/2002 | Ljungmann |

(Continued)

FOREIGN PATENT DOCUMENTS

DE 1 182 253 11/1964

(Continued)

OTHER PUBLICATIONS

Database WPI Section PQ, Week 200139, Derwent Publications, Ltd., London, GB; AN2001-373303, XP002250702 (1 page).

(Continued)

*Primary Examiner*—Jyoti Nagpaul
(74) *Attorney, Agent, or Firm*—Ventana Medical Systems, Inc.; Richard D. Schmidt

(57) ABSTRACT

An apparatus and method for selecting and dispensing coverglasses over specimens on slides for the purpose of viewing specimens through a microscope. The selecting device contains a suctioning mechanism for picking up a coverglass from a stack of coverglasses. It also contains the ability to bend the coverglass to assist in separating the coverglasses. The apparatus further contains a matched barrier to eliminate any coverglasses that may stick to the selected coverglass. The selecting device also contains spring members which aid in the dispensing of the coverglass. After the suctioning mechanism releases the coverglass, the spring members exert a force onto the coverglass to insure that it is released from the selecting device and placed onto the slide. After placement of the coverglass onto the slide, capillary action pushes air bubbles out from underneath the coverglass.

19 Claims, 13 Drawing Sheets

U.S. PATENT DOCUMENTS

| | | |
|---|---|---|
| 2003/0047863 A1 | 3/2003 | Lang et al. |
| 2004/0092024 A1 | 5/2004 | Reinhardt et al. |

FOREIGN PATENT DOCUMENTS

| | | |
|---|---|---|
| EP | 1 052 497 A2 | 11/2000 |
| JP | 04122595 | 4/1992 |
| JP | 07242350 | 9/1995 |
| JP | 09325105 | 12/1997 |
| WO | WO 95/20176 | 7/1995 |
| WO | WO 00/37986 | 6/2000 |

OTHER PUBLICATIONS

Product Brochure, The New Protocol in Staining Technology, Fisher Healthcare (1 page).

Product Brochure, Hacker Instruments & Industries, Inc., Coverslippers & Stainers, www.hackerinstruments.com/coverslippers.htm (3 pages).

Product Brochure, Sakura Tissue-Tek SCA Coverslipper, 1998 (5 pages).

Product Brochure, Sakura Tissue-Tek SCA Coverslipper (7 pages).

Product Brochure, Shandon Laboratory Equipment 1998-1999 (15 pages).

Product Brochure, Advanta CV and Advanta AS (1 page).

Product Brochure, Advanta CV/AS, Vision Instruments Ltd. (2 pages).

Product Brochure, Leica CV 5000, The efficient robotic coverslipper for histology and cytology laboratories (4 pages).

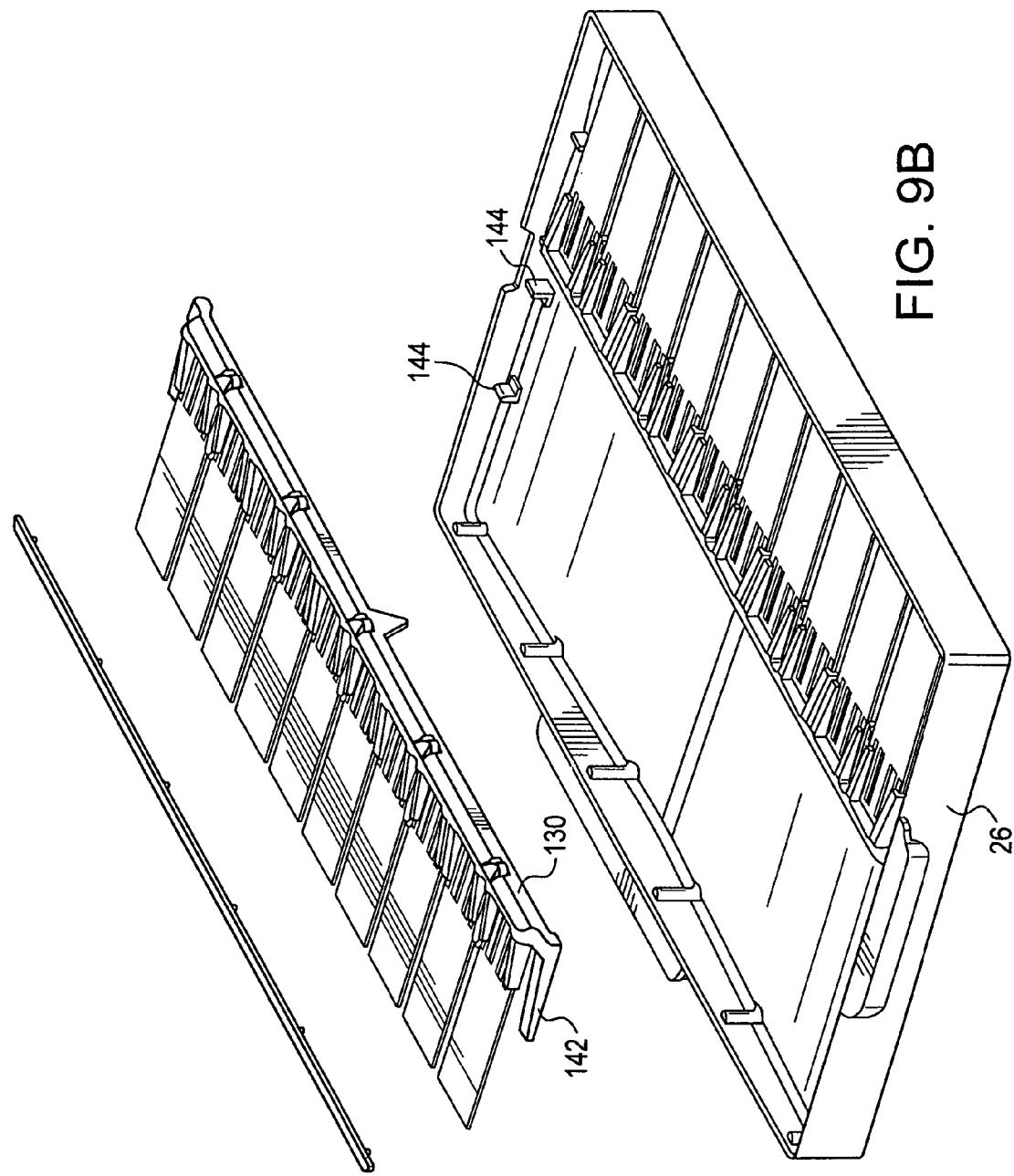

METHOD AND APPARATUS FOR AUTOMATED COVERSLIPPING

This is a divisional of U.S. patent application Ser. No. 10/424,335, filed Apr. 25, 2003, now U.S. Pat. No. 7,271,006 which claims the benefit of U.S. Provisional Patent Application No. 60/375,925, filed on Apr. 26, 2002, the contents of which applications are incorporated by reference herein.

FIELD OF THE INVENTION

This invention relates to a method and apparatus for automatically covering a specimen to be examined on a microscope slide with a tissue coverglass.

BACKGROUND OF THE INVENTION

Scientists examine numerous specimens placed on slides using microscopes. Typically, a specimen is covered with a thin transparent coverglass. This is done for several reasons. The coverglass can flatten the specimen so that the specimen is in the same viewing plane, thereby allowing one to view the specimen better. The coverglass provides protection for the specimen from the objective lens of the microscope should the lens be placed too closely to the slide. The coverglass may further provide a housing structure or an area by which the specimen will be permanently retained on the slide. The coverglass, in combination with a liquid adhesive, also helps to preserve the specimen for archiving purposes.

The coverglass is typically a thin, rectangular, square or round piece of glass or plastic which is placed in direct contact with and over the specimen on the slide. The coverglass comes in a variety of sizes and shapes. One example of the coverglass has dimensions of about 1"×2" and 0.005" to 0.009" thick. They are packaged stacked in a vertical pile. This stacking presents a problem: the coverglasses are difficult to handle and separately remove from the stack since they are fragile and may stick together easily. Typically, to remove one coverglass from the stack, a considerable amount of bending moment is applied at the middle of the coverglass. For example, some prior art systems, such as shown in U.S. Pat. No. 5,989,386 (Elliott) use two suction cup devices on a coverglass, placed on both sides of the middle of the coverglass. The suction cups thereafter bend the coverglass, creating great stress in the middle of the coverglass in order to separate the coverglass from the stack of coverglasses. However, this action results in numerous coverglasses breaking because they are very fragile and the force applied was greater than the stability of the glass. The bending force causes a disproportionate amount of stress at the center of the coverglass. Furthermore, the bending action did not guarantee that only one coverglass was selected.

After selecting a single coverglass, the coverglass is then placed over the specimen on a slide in the presence of a liquid adhesive. This presents other problems. For example, it is important that there are no air bubbles trapped under the coverglass when it is placed onto the slide. Also, it is important not to harm the specimen in any way when positioning the coverglass onto the slide. One way to apply the coverglass was to place the coverglass on the slide, and then apply pressure onto the coverglass compress to remove trapped air bubbles. In addition, handling and separating the coverglasses at times can charge them with static electricity. Electrostatic forces can hold the coverglass to the suction cups even after turning the mechanism off, making it difficult to apply the coverglass to the slide. Moreover, the compression of the coverglass to remove air bubbles may cause the adhesive on the tissue sample to expel outward, thereby potentially contaminating other slides or other portions of the machine.

Thus, there exists a need to provide a better automated coverslipper that avoids the problems of prior art automated coverslippers.

SUMMARY OF THE INVENTION

In one embodiment, the invention is directed to a method and apparatus for removing at least one coverglass from a stack of coverglasses. In one aspect, the method and apparatus removes the coverglass using a single sealing member. The sealing member forms a seal along a circumference of the coverglass (e.g., providing a seal along or proximate to the edges of the coverglass). The coverglass may then be bent using the single sealing member. The bending may include deforming the coverglass so that the coverglass has a constant or near constant bend radius (i.e., the curvature of the coverglass is approximately constant along the edge, preferably the longitudinal edge, of the coverglass). In one embodiment, the bending of the coverglass is performed using the sealing member in combination with a suction block. The suction block may be used as a support for the coverglass during deformation and may be shaped with a constant curvature so that when the coverglass is deformed, its shape has a constant (or substantially constant) bend radius. Greater separating force is generated along the edges while not overstressing other areas, which is less likely to break the coverglass and more likely to result in a separation of the coverglass. In this manner, the apparatus and method enable the separation of a coverglass from the stack of coverglasses. After selection of a coverglass, the stack of remaining coverglasses may be lowered and a curved barrier that may be matched to the shape of the bent coverglass wipes beneath the selecting device to remove any clinging coverglasses that may be present. Any coverglasses wiped from beneath the selected one will be placed back onto the remaining stack.

Another embodiment is an automatic device and method for dispensing the coverglass onto the slide after the coverglass has been successfully removed from the stack. In one aspect, a liquid for adhering the coverglass is applied along an edge of the slide. In a first preferred embodiment, the liquid is an adhesive-activating liquid such as xylene or toluene, that functions to dissolve a pre-applied layer of adhesive on the coverslip. In a second preferred embodiment, the liquid is itself an adhesive, and is applied to a standard coverslip. The liquid may be in the form of drops or a continuous bead. An edge of the coverglass is then released (e.g., placed, via gravity) at an edge of the specimen (preferably at the long end of the slide) proximate to the liquid previously placed on the slide. Thus, the cover glass and the surface of the slide may form a "V" shape. In one embodiment, while one edge of the coverglass is touching the slide, the opposite edge is lowered (though not to the point where the opposite edge touches the slide). Thereafter, the remaining edge of the coverglass is released, allowing it to settle onto the sample tissue on the slide. In this manner, there is a continuous bead of fluid at the intersection between the coverglass and the slide.

In the embodiment wherein the coverglass is held via a suctioning mechanism, the suctioning mechanism is turned off allowing the coverglass to fall onto the slide via gravity. Spring member(s) may be located in the flexible backing plate. The spring member(s), compressed by the force of the coverglass against the flexible backing plate, exert a small restoring force on the coverglass when it is released insuring the disengagement of the coverglass from the sealing member. Moreover, the coverglass may be held by a conductive sealing member. In this manner, the sealing member may be connected to ground, thereby reducing the possibility of static electricity causing the coverglass to cling after the suctioning mechanism is turned off.

Still another aspect of the invention is a cartridge for a stack of coverglasses. The cartridge may comprise an open-ended substantially rectangular box, the open end being substantially concave along at least one of its long axes, one or more alignment lips for aligning and then guiding the cartridge into position, one or more detents for locating one or more plungers thereby securing the cartridge in place, and one or more apertures in the bottom end of the box for allowing entry of a fork to push the coverglasses into position. The alignment lip may be located adjacent to the closed end of the box. Moreover, the detents may be located on the alignment lip. In addition, the cartridge may comprise a touch memory button. Further, the cartridge may comprise at least one cutout, the cutout being located in an interior of the rectangular box where two of the sidewalls meet.

These as well as other features and advantages of the present invention will become apparent to those of ordinary skill in the art by reading the following detailed description, with appropriate reference to the accompanying drawings.

BRIEF DESCRIPTION OF THE FIGURES

FIG. 9b is a partially exploded view of the tray in FIG. 9a.

DETAILED DESCRIPTION OF PREFERRED EMBODIMENTS

Figure 1:
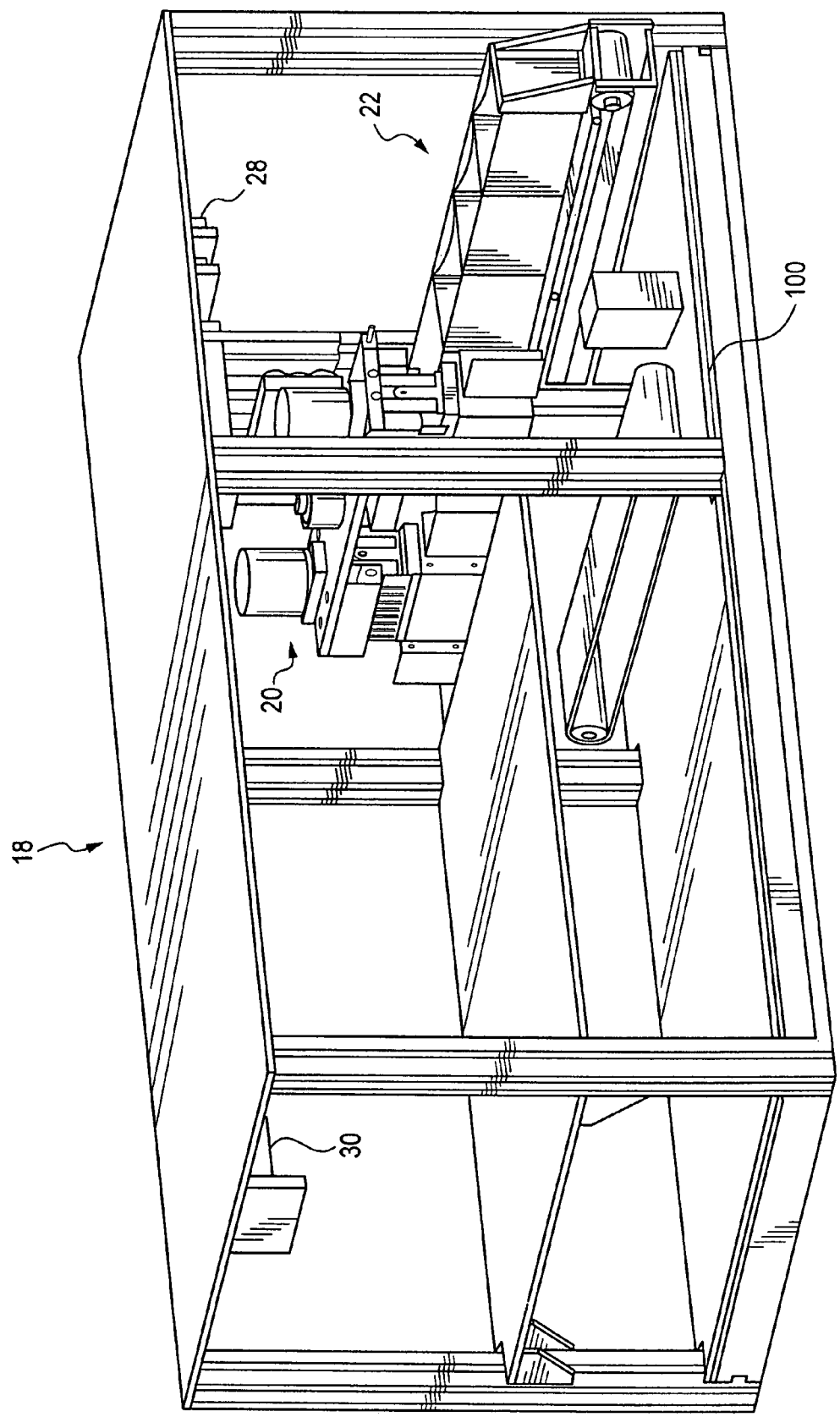
FIG. 1 is a frontal perspective view of the automated coverslipper apparatus.

Referring to FIG. 1, there is shown a perspective view of an automated coverslipper module 18. The automated coverslipper module 18 includes a head portion 20 (see e.g. FIG. 3), a cartridge supply and dispense device 22 (see e.g., FIG. 7), and a flat portion 24 upon which a tray 26 (see e.g., FIG. 9) sits. The head portion 20 moves in one direction using motor 28 to move along rail 30.

Figure 2:
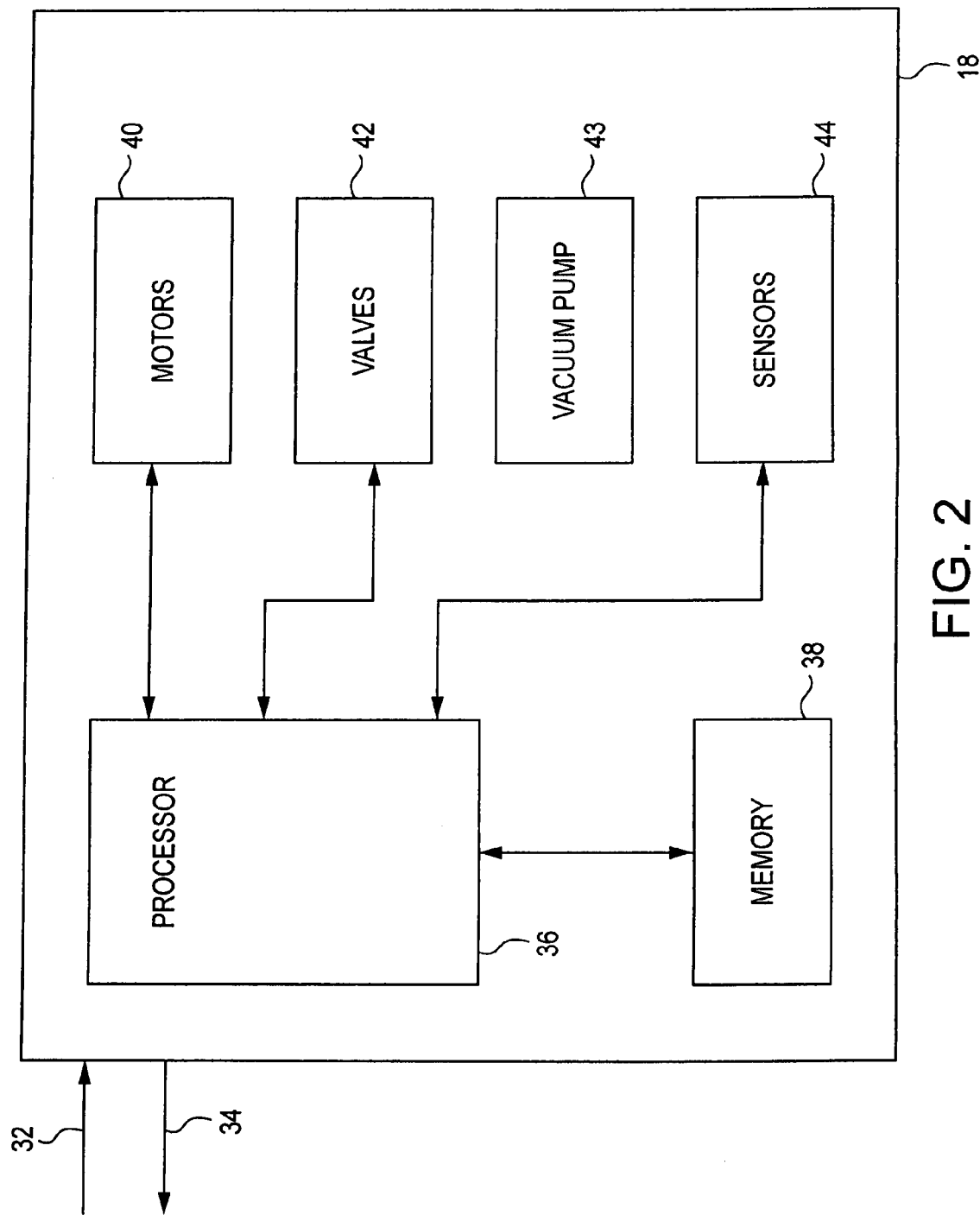
FIG. 2 is a block diagram of the automated coverslipper apparatus.

Referring to FIG. 2, there is shown a block diagram of the automated coverslipper module 18. The automated coverslipper module includes inputs/outputs 32, 34. In one embodiment, the automated coverslipper module is integral with other components of a tissue staining instrument (i.e., contained within a single device). See U.S. Patent Application No. 60/372,506 filed on Apr. 15, 2002 and incorporated by reference in its entirety. In an alternative embodiment, the automated coverslipper module may be a physically separate, yet electronically connected device, interacting with other modules of a tissue staining instrument. Examples of tissue staining machines are disclosed in U.S. Pat. No. 6,045,759 and U.S. Pat. No. 6,296,809, both of which are hereby incorporated by reference in their entirety.

The inputs 32 and outputs 34, which are discussed below, may communicate with a central processor (not shown) of the automated tissue staining machine. Examples of inputs include control of motors, such as motor 28 in FIG. 1 (for moving head assembly in the x-direction), motor 46 in FIG. 3 (for moving the head assembly in the z-direction) and motor 92 in FIG. 6 (for moving the stack of coverglasses upward and downward), each described subsequently. Examples of outputs include (1) an indication of the dispensing of liquid onto the slide (e.g., glue and/or solvent(s)); (2) an indication of pumping of the liquid; (3) an indication whether a vacuum is achieved; and (4) an indication that the sealing member assembly (see e.g., FIGS. 4 and 5) is flexed or twisted.

The automated coverslipper module includes a processor 36 and memory device 38. As described in more detail below, the automated coverslipper module 18 further includes motors 40 (such as 28 and 46, shown in FIGS. 1 and 3), valves 42 (such as for controlling the dispense of the liquid through nozzles 54, shown in FIG. 3), vacuum pump 43 and sensors 44 (such as sensors shown in FIGS. 7 and 9). The processor 36 may be a microprocessor executing commands either received directly from the inputs/outputs or stored in the memory device. The memory device 38 may include either a permanent memory device (such as a read only memory), a temporary storage device (such as a random access memory) or a combination of both. In one embodiment, the memory device 38 may contain instructions for operating the automated coverslipper module 18, the instructions being sent by the input 32 and temporarily stored in the memory device 38. Alternatively, the memory device 38 may permanently store the instructions for operation of the motors 40, valves 42, and sensors 44 with the processor 36 accessing the instructions. This and other arrangements described herein are shown for purposes of illustration only, and those skilled in the art will appreciate that other arrangements and other elements (e.g., types of processor, memory devices, inputs, outputs, etc., whether or not separately known in the prior art) can be used instead, and some elements may be omitted altogether.

Figure 3:
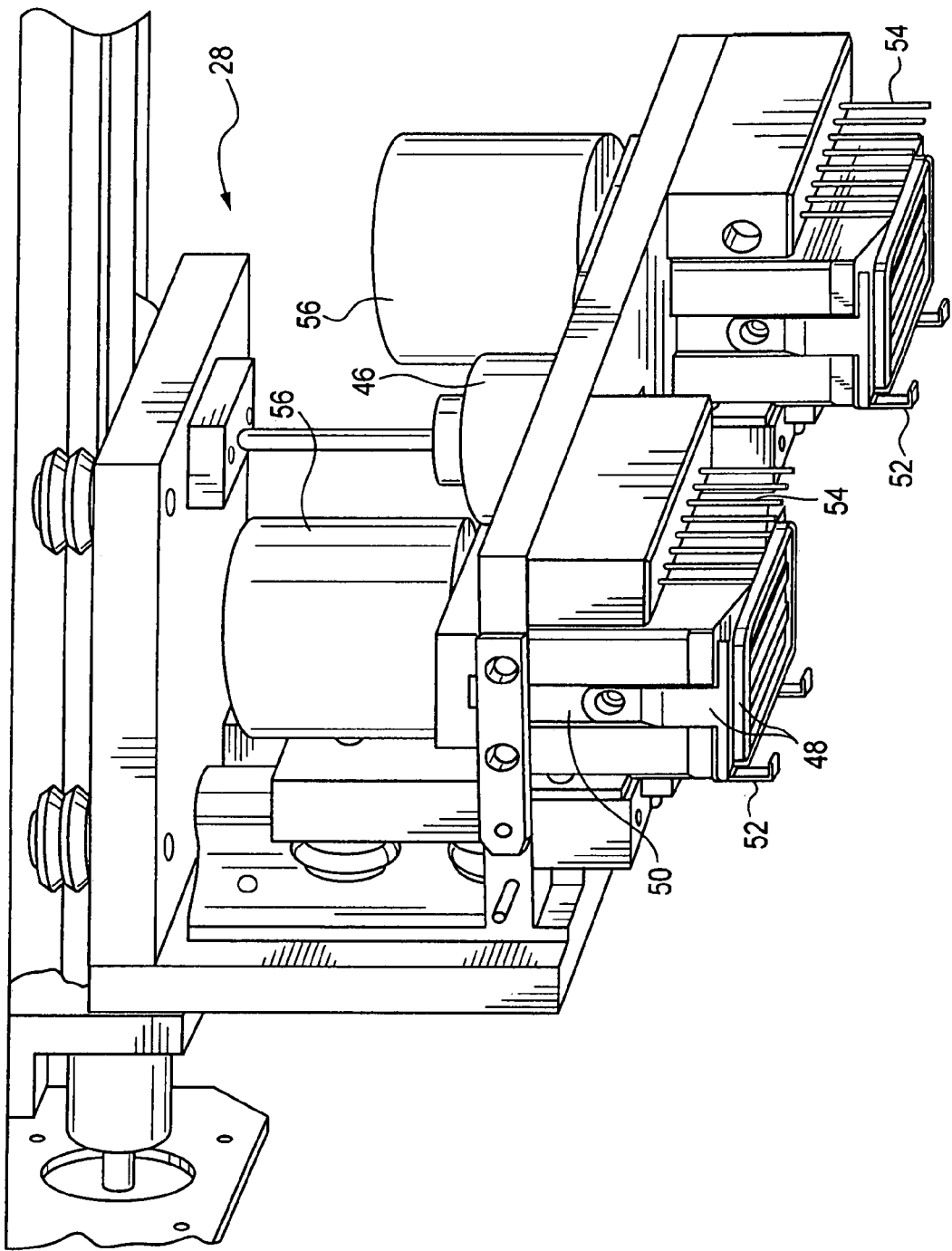
FIG. 3 is a perspective view of the head portion of the automated coverslipper of FIG. 1.

Referring to FIG. 3, there is shown a perspective view of the head portion of the automated coverslipper module. The head portion 20 includes dual head assemblies, one for each side of the tray 26 (as shown in FIG. 9). The head portion 20 may include a single head assembly or multiple head assemblies, depending on the needs of a particular system. Further, the head assembly may be moved within the automated coverslipper module 18. In one embodiment, the head assembly may be moved in two directions: the x-direction (by motor 28, as discussed above); and the z-direction (by motor 46). In an alternate embodiment, the head assembly may be moved in the x-, y-, and z-directions.

The head assembly includes: (1) a sealing member assembly 48 (see e.g., FIGS. 4 and 5); (2) a support block 50 (see e.g., FIG. 4); (3) at least one spacer arm 52, and preferably two spacer arms; (4) at least one nozzle 54 for dispensing fluid and associated tubing and valves; (4) device for moving the sealing member assembly 56; and (5) a motor 46. As shown in FIG. 3, there is a plurality of nozzles 54 for dispensing liquid. In one aspect, the nozzles dispense approximately 50 μL of liquid. However, more or less fluid may be dispensed. The nozzles 54 may be composed of a variety of materials depending on the fluid being dispensed. In one aspect, the liquid dispensed is mounting media (e.g., a combination of glue and a solvent such as xylene). In another aspect, the liquid dispensed is a solvent such as xylene. In a preferred embodiment, the nozzles 54 are composed of stainless steel with an outer diameter of Teflon® coating. The nozzles are connected to a liquid container via tubing (not shown) and at least one valve 42 in FIG. 2. The transfer of liquid to the nozzles 54 is controlled by processor 36 which controls the least one valve 42.

In one embodiment, the valve 42 includes a "suck back" feature. Nozzles 54 may, after dispensing of liquid, include a hanging drop. This hanging drop is unwanted since it may fall onto one of the samples on the slides. In order to remove the hanging drop, a "suck back" feature is employed. The "suck back" feature, in operation, reverses the flow of the liquid, thereby pulling excess fluid back into nozzles 54. The "suck back" feature may be implemented in a variety of ways. One example is by using a membrane which is connected to the tubing supplying liquid to nozzles 54. An air cylinder may activate the membrane in order to pull a hanging drop from nozzles 54. A commercially available membrane is sold by SMC Corporation, model number LV23-2S06. Another example is by using a secondary pump to pump the hanging drop from the edge of nozzles 54. Still another example is by modifying valve 42. In one embodiment, the valve 42 is a one-way solenoid valve, so that liquid flows from the container to the nozzles. The solenoid valve may be replaced with a two-way valve so that the valve may send fluid to the nozzles 54 and also pull fluid from the nozzles 54. The amount of fluid which may be pulled from the nozzles is a small amount, typically no more than a few drops to account for any drops hanging on nozzles.

The device 56 for moving the sealing member assembly is, in one embodiment, an air cylinder. The air cylinder moves the sealing member assembly 48, and in particular the brackets 66. As disclosed subsequently with respect to FIG. 4, the brackets 66 may be moved upward in order to separate a coverglass from the stack of coverglasses.

Figure 4:
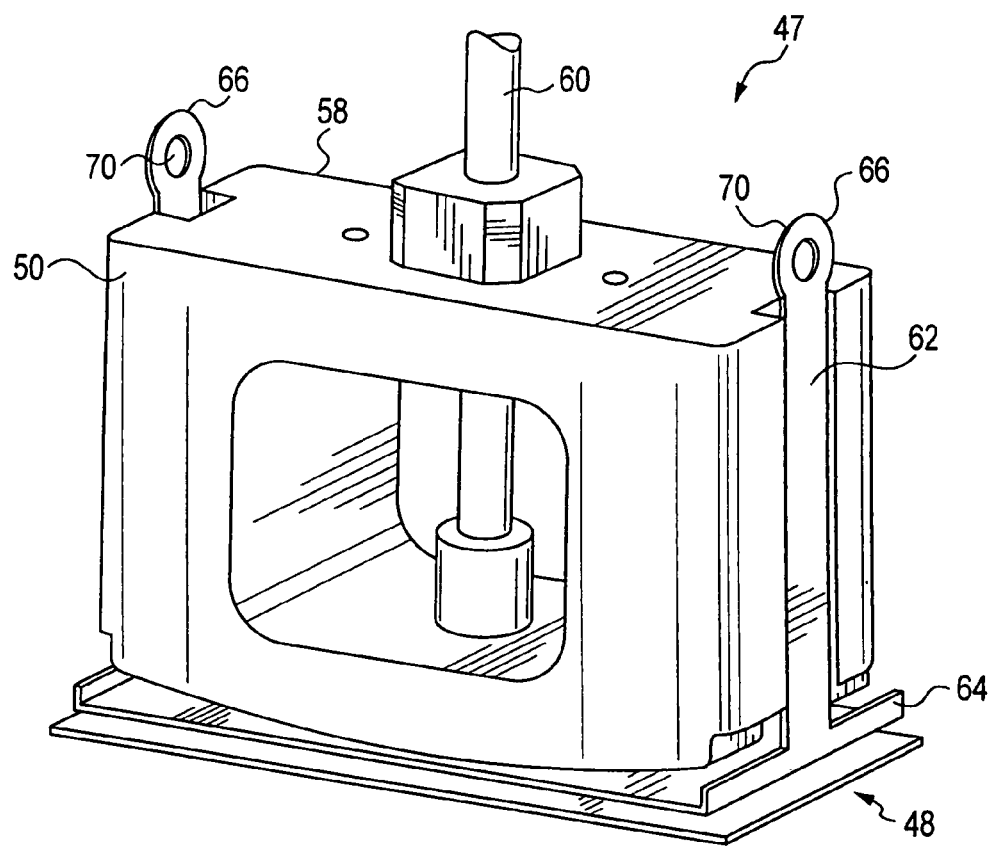
FIG. 4 is a perspective view of one embodiment of the support block and sealing member assembly shown in FIG. 3.

Referring to FIG. 4, there is shown a perspective view of the coverslip gripper assembly 47 comprising the support block 50 and sealing member assembly 48 for the head portion 20 (shown in FIG. 3). Support block 50 may be composed of a variety of shapes. As shown in the embodiment of FIG. 4, support block 50 is of rectangular shape having the inner part 58 removed to allow space for the tubing 60 (or other conduit) of the vacuum generator 43 to be inserted. In an alternative embodiment, a conduit comprising a cylindrical hole may be drilled or otherwise formed into the support block for communication of vacuum. The support block 50 may be made from machinable polymer, ceramic or metal materials. A complete seal, air tight connection should be made between the coverglass and the sealing member 72 (shown in FIG. 5). The lower portion 62 of support block 50 is of a curved shape. In a preferred embodiment, the curved shape is a constant (or nearly constant) radius. As discussed subsequently, the flexible backing plate 64 of the sealing member assembly (while holding a coverglass 68) is bent to conform to the lower portion 62 of support block 50.

Figure 5:
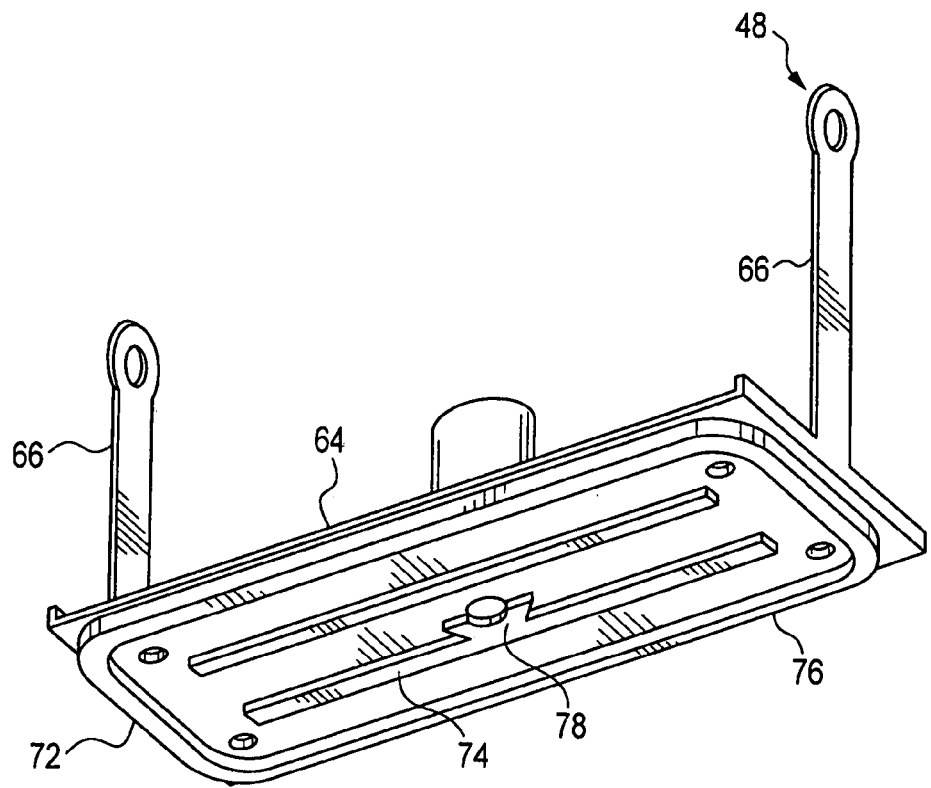
FIG. 5 is a bottom perspective view of the sealing member assembly showing shown in FIG. 4.

Referring to FIG. 5, there is shown the sealing member assembly 48 which includes flexible backing plate 64 and brackets 66. The sealing member assembly 48 may be mounted to support block 50 either via the flexible backing plate 64 (e.g. to the lower portion of support block) or by the brackets 66 positioned on each side of the support block 50. The brackets 66 include holes 70 for connection. The brackets 66 may be made from metal materials or they may be made from the same materials as the flexible backing plate 64. In the preferred embodiment, the brackets 66 and the flexible backing plate 64 are one integral piece with no connections between them. In an alternative embodiment, the brackets 66 and the flexible backing plate 64 comprise separate pieces connected together. The coverglass 68 is selected and held by flexible backing plate 64, as described in more detail subsequently.

A second preferred embodiment of the coverslip gripper comprises a combination of the sealing member assembly 48 and the support block 50. The major components, i.e., support block 50, flexible backing plate 64, brackets 66, and sealing member 72 may be manufactured as one article through processes well-known in the art, such as injection molding. The coverslip gripper would then also have the function of the sealing member 72 as the sealing member would be integral with the flexible backing plate 64.

A bottom view of the sealing member assembly is shown in FIG. 5. Connected underneath the flexible backing plate 64 is a sealing member 72. The sealing member 72, in the most preferred embodiment, is elastomeric and may be compressed upon contact with coverglass 68. The sealing member 72 may also be composed of other materials, such as a soft plastic. The sealing member 72 may be less than 0.25" thick. The flexible backing plate 64 may be a flexible material (such as sheet metal stainless steel backing) that the elastomeric sealing member 72 is bonded to. In a preferred embodiment, the flexible backing plate 64 is rectangular shaped with size comparable to the coverglass 68. The sealing member 72 may be of any shape which covers the geometric center of the coverglass, but preferably covers at or proximate to the perimeter of the coverglass. As described subsequently, the sealing member 72 allows for an evenly distributed force to a perimeter of the coverglass. In the most preferred embodiment, conductive material may be used for the sealing member 72 which is adhered or affixed to flexible backing plate 64. Sealing member 72 may then be grounded, either by connection to the flexible backing plate 64 or connection directly to ground to eliminate static electricity buildup on the sealing member 72. Adding carbon or other conductive materials to the rubber mixture of the sealing member 72 will make it conductive which can then be grounded, solving the problem of electrostatic charge buildup since the sealing member 72 will discharge the static charge. This may reduce the possibility of the selected coverglass 68 from adhering to the flexible backing plate 64 after dispensing of the coverglass 68. This also may reduce the possibility of a second coverglass adhering to the selected coverglass 68. The sealing member 72 is positioned proximate to the edges of the flexible backing plate 64. For a rectangular flexible backing plate 64, the sealing member 72 is of rectangular shape with rounded corners.

Supports 74 of the sealing system are mounted inside the perimeter of the sealing member 72 underneath the flexible backing plate 64. In a preferred embodiment, the supports 74 extend nearly to each distal end of the sealing member 72. The preferred embodiment places two supports spaced equally inside the perimeter of the sealing member 72. Alternative embodiments may use more or less supports of varying lengths placed within the sealing member 72. The supports 74 provide rigidity and minimize the deformation of the coverglass 68 when suctioning is taking place. This reduces "cupping" of the coverglass which may produce air bubbles after placing the coverglass on the specimen. The supports 74 also provide a firm structure against which the coverglass 68 may maintain its original form except for the axis of bending. Moreover, the supports 74 provide rigidity for the coverglass 68 that is selected from the stack 182. The supports 74 may be made of the same elastomeric material of which the sealing member 72 is made.

Sealing member 72 may provide a complete seal around the top coverglass 68 allowing the vacuum pump 43 to produce an equal force to the whole area of the coverglass 68 when suctioning it from the stack 182. One embodiment of the positioning of the vacuum passage 78 may be in the center of the flexible backing plate 64 as shown in FIG. 5. The vacuum passage 78 may be a single, small round shape. Alternatively, the vacuum passage 78 may be a series of holes all connected to vacuum.

Figure 6:
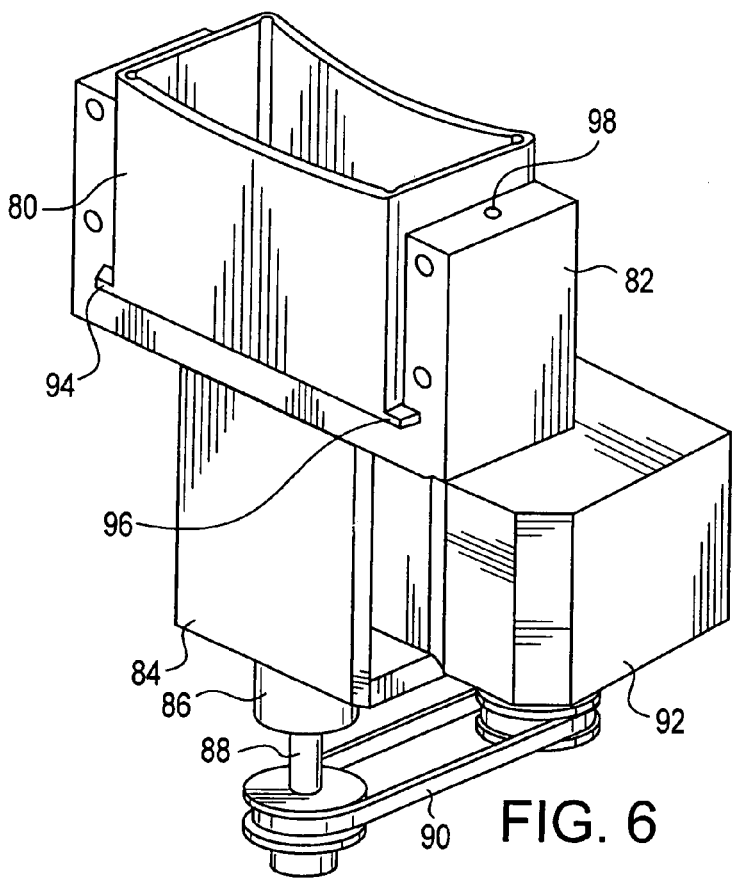
FIG. 6 is a perspective view of the cartridge, cartridge holder, and tuning fork, lead screw, shaft, belt and motor.
Figure 8A:
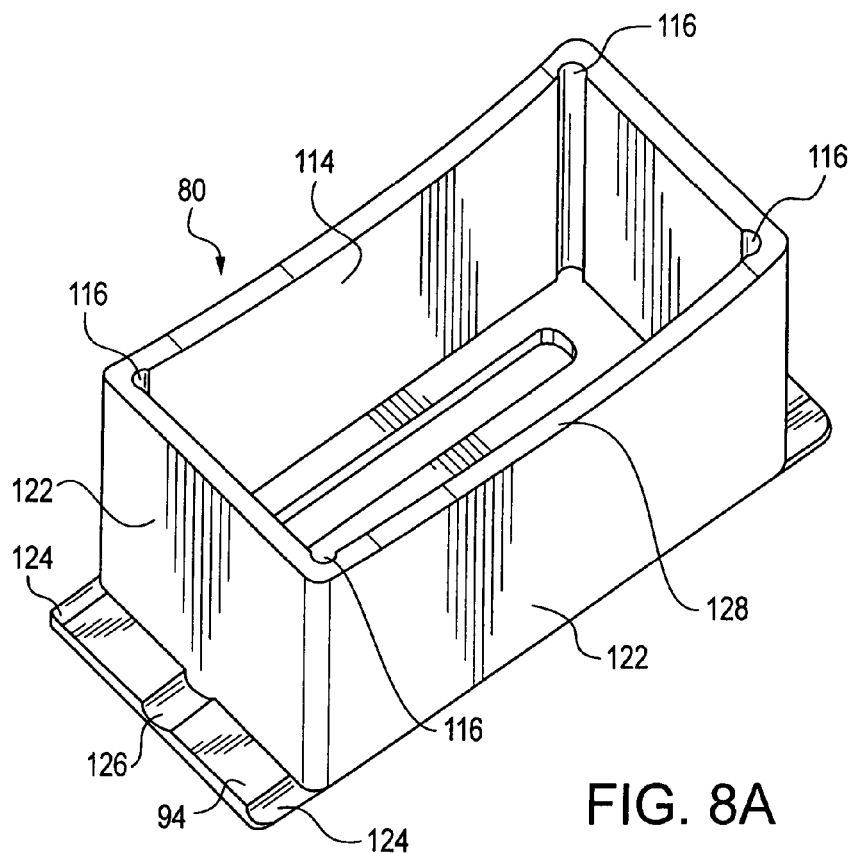
FIG. 8a is a top perspective view of the cartridge of FIG. 6.
Figure 8B:
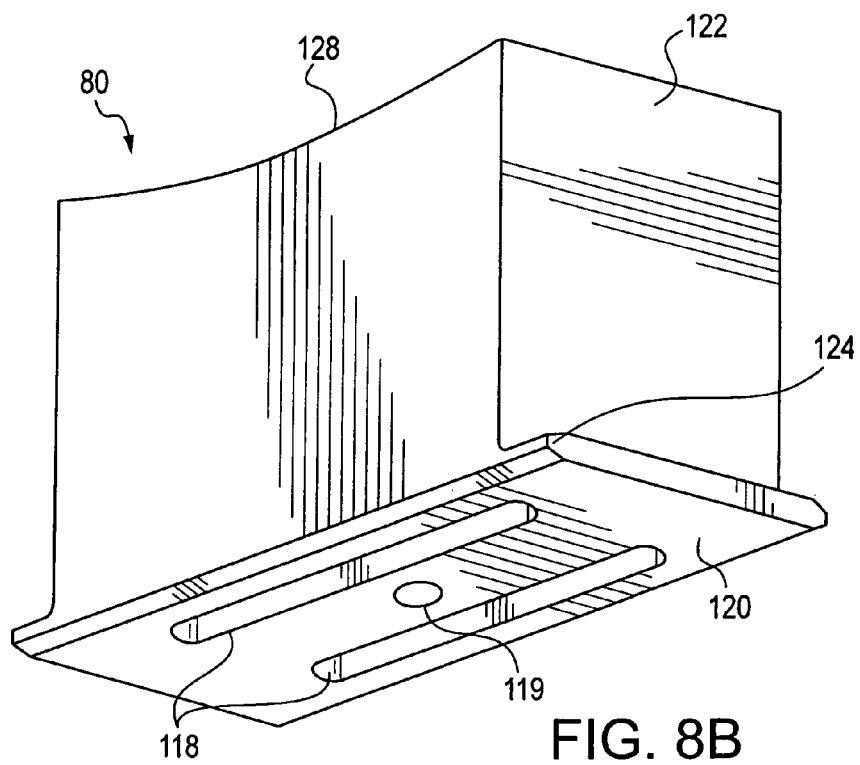
FIG. 8b is a bottom perspective view of the cartridge of FIG. 6.

Referring to FIG. 6, there is shown a perspective view of the cartridge 80, cartridge holder 82, and fork 84, lead screw 86, shaft 88, belt 90 and motor 92. A stack of coverglasses (not shown) is contained within cartridge 80. Further, the cartridge 80 is held within cartridge holder 82. The cartridge holder acts to secure the cartridge in at least one direction. In one embodiment, the cartridge 80 has at least one alignment lip 94 (and preferably two lips, as shown in FIGS. 6, 8a and 8b) for insertion in at least one slot 96 (and preferably two slots, as shown in FIG. 6). Further, the cartridge holder 82 may include a plunger 98 in one or both sides of the cartridge holder in order to engage at least one slot (and preferably two slots, see FIG. 8a). The cartridge holder 82 thus may serve as an x-y-z orienting device.

The coverglasses should contact the sealing member assembly 48, either by moving the sealing member assembly 48 to the coverglasses, by moving the coverglasses to the sealing member assembly 48, or a combination of both. In one embodiment, the coverglasses in the cartridge holder 80 are raised a fixed amount to the sealing member 72 so that the top coverglass may be selected. A motor 92, belt 90, shaft 88, lead screw 86 and fork 84 are shown in FIG. 6 for moving the fork upward and downward. The fork, upon being raised, is inserted into slotted holes 118 (shown in FIG. 8b) in a bottom portion of the cartridge 80. The fork 84, upon entry into the cartridge 80, raises the stack of coverglasses. The motor 92 moves the fork 84 upward until the top coverglass contacts the suction sup assembly 48. The motor 92 thereafter stalls. After a predetermined time, the motor 92 is reversed and the fork 84 is moved downward, thereby moving the stack of coverglasses.

Figure 7:
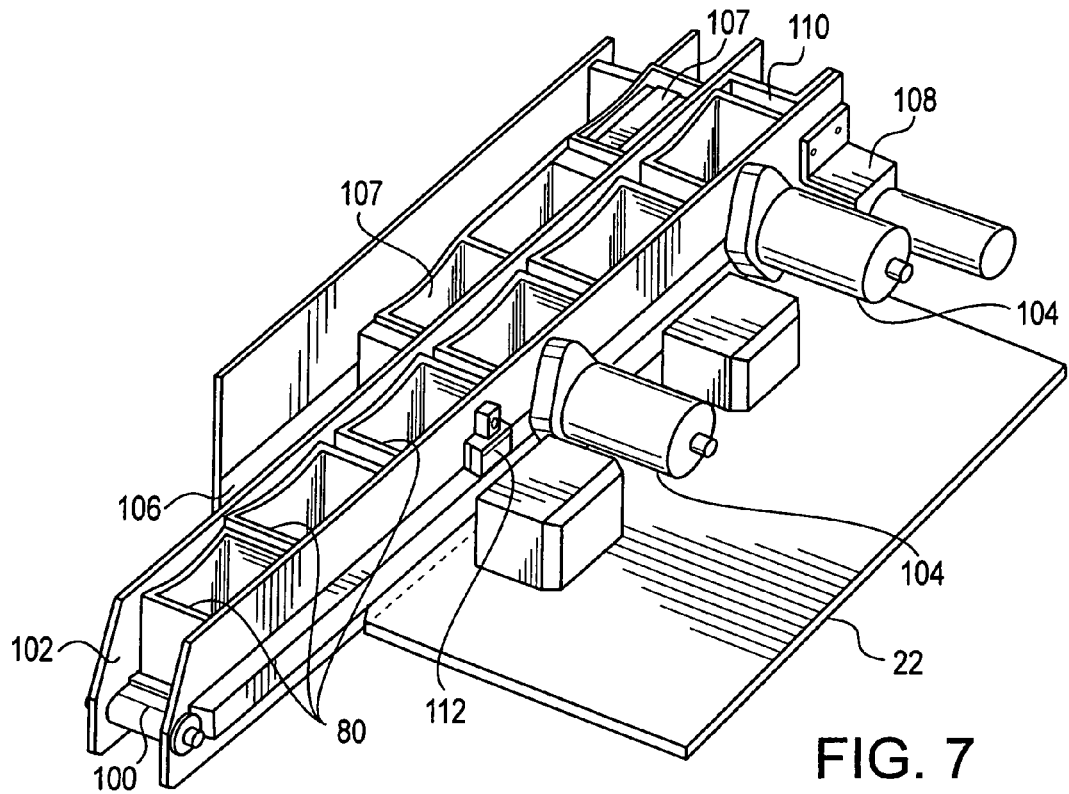
FIG. 7 is a perspective view of the cartridge supply and dispense device of FIG. 1.

Referring to FIG. 7, there is shown a perspective view of the cartridge supply and dispense device 22. Cartridges 80 are fed via a conveyer 100 and are placed within channel 102. Motor 108 is used to rotate conveyor 100 so that cartridges are lined up against stop 110, as shown in FIG. 7. In the embodiment shown in FIG. 3 with two head assemblies, there are two stations 107 in which the cartridges 80 are placed. At each station 107, the cartridges may be held by cartridge holder 82, as discussed previously. When a cartridge in the cartridge holder 82 needs to be moved, as discussed subsequently, piston 104 is used. Piston 104 pushes a cartridge on conveyor 100 which in turn pushes the cartridge in the cartridge holder 82 onto conveyor 106 for disposal. Conveyor 106 may then be moved to dispose of cartridge. In one embodiment, a single motor (for example, motor 108) may operate both conveyor 100 and conveyor 106 via a cam (not shown) linking the conveyors 100 and 106. Alternatively, conveyor 100 and conveyor 106 may be operated using separate motors.

In order to determine if a cartridge should be placed on conveyor 100, sensor 112 may be placed proximate to conveyor 100. Sensor 112 may be an optical sensor for sensing if a cartridge is adjacent or proximate to sensor 112. If the sensor 112 senses that no cartridge is present, processor 36 is notified and a message is sent via output 34 to notify operator to place cartridges onto conveyor 100.

Typically, a cartridge is used until it is believed to be empty of coverglasses or until it is determined that the coverglasses in the cartridge are damaged. In one embodiment, to determine when to replace a cartridge, the sealing member assembly 48 is used. During ordinary operation, motor 92 moves the stack of coverglasses so that the top coverglass contacts the flexible backing plate 72. After contact with a coverglass and after turning on the suction pump, a vacuum seal should be formed. This seal may be sensed by sensor 44. In the event that sensor 44 does not sense that a seal has formed, the processor 36 is notified. Failure to seal may indicate either that the cartridge is empty of coverglasses or that the coverglasses (either attached to flexible backing plate 72 or on top of the stack) are broken or damaged. The processor commands the motor 92 to lower the stack of coverglasses. Motors 28 and 46 move the head assembly to a place where the tray 26 is not below and remove the vacuum from the sealing member assembly. In this manner, if a damaged coverglass is clinging to the sealing member assembly 48, it may be removed without falling onto, and subsequently damaging, any tissue samples. Motors 28 and 46 thereafter move the head assembly back into position so that motor 92 may raise the stack of coverglasses to contact the flexible backing plate 72. If a vacuum seal may not be generated yet again, this process of moving the head assembly using motors 28 and 46 to a predetermined position and removing the vacuum from the sealing member assembly 48 may be repeated again.

In a second preferred embodiment cartridge 80 has a self-contained read-write memory device attached to it for keeping track of data related to the cartridge. The memory device may be a "touch memory" device such as an EPROM sold by Dallas Semiconductor as the DS1985 F5 16 Kbit add-only touch memory device. Other memory devices may be used to store the information and allow the end user to retrieve the information, such as an RFID (Tag-It HF-I Transponder Inlay Rectangle, Texas Instruments, Dallas, Tex.). As shown in FIG. 8b, the touch memory device 119 is incorporated into the cartridge 80 and contains information pertaining to the contents of the cartridge, such as the number of coverslips remaining, type, lot number, expiration, and related information. The memory device enables communication between the cartridge and the system processor, thus adding an element of intelligence to the overall system. The data feature includes memory device 119 mounted on the cartridge at a position that will not interfere with coverslip loading and unloading operations of the apparatus, an on-board PIC microcontroller contained within the automated coverslipper for running the operations of the device while being in communication with the memory device, and a contact reader for the data button. A similar memory device is described in U.S. Ser. No. 08/995,052, filed Dec. 19, 1997, incorporated herein by reference in its entirety. Its primary function is to initialize the system for each new coverslip cartridge that is presented to the automated coverslipper, and to keep track of the number remaining. The memory device contains information such as the number of coverslips, whether they are pre-glued or not, date of expiration, lot no., etc. In operation, the memory device is initially read-in the number of coverslips in the cartridge when loaded with coverslips at the factory. When the cartridge is loaded into feed position on the coverslipper, contacts (not shown) on the cartridge holder 82 contact the memory device, or the memory device 119 itself makes direct electrical contact with a memory reader (not shown) which is built into the upper stage so that as the cartridge is slid into position it contacts the memory reader. The microcontroller then tracks the number of coverslips left in the cartridge until the cartridge is empty. The on-board microcontroller will then notify the user through an interface as to how many coverslips are left. The on-board microcontroller writes the number of coverslips to the memory after each dispense step so that in the event of a power loss or instrument shutdown, the total number of coverslips remaining in that particular cartridge is not lost.

Referring to FIGS. 8a and 8b, there are shown are a top perspective view and bottom perspective view (respectively) of the cartridge of FIG. 6. The cartridge includes: an open-ended box with a bottom 120 and sidewalls 122. The bottom 120 and sidewalls 122 form an interior 114. In a preferred embodiment, the open-ended box is rectangular in shape. This rectangular shape is so that the box may house the coverglasses, which are typically rectangular in shape. However, the cartridge 80 may be of any shape in which to house the coverglasses.

The cartridge further includes one or more alignment lips 94. The alignment lip 94 may be on one or more sides of the bottom 120 of the cartridge 80. As shown in FIGS. 8a and 8b, there are two alignment lips, each located adjacent to the closed end of the box. The alignment lip 94 may be used in conjunction with slot 96, as discussed above, to engage the cartridge 80 into cartridge holder 82. The alignment lip 94 may include at least one narrower portion 124. As shown in FIGS. 8a and 8b, the narrower portions 124 are at the edges of alignment lip 94. The narrow portions 124 facilitate entry of the alignment lip 94 into slot 96. In addition, the alignment lip 94 may include at least one detent 126. The detent 126 may be placed at any portion of the alignment lip 94. In a preferred embodiment, the detent 126 is placed in the center of alignment lip 94, as shown in FIG. 8a. As discussed previously, detent 126 engages plunger 98 of cartridge holder 82.

The cartridge 80 further may include one or more apertures in the bottom. The one or more apertures in the bottom end of the box for allowing entry of a fork to push the coverglasses into position. In a preferred embodiment, the bottom 120 includes two apertures which are oblong in shape. In this manner, fork 84 may enter bottom 120 in order to raise the stack of coverglasses contained in interior 114 of cartridge 80.

In addition, the open end of the cartridge 80 may be substantially concave or curved along one of its axis. In a preferred embodiment, the open end of the cartridge is curved along its long axis. Specifically, as shown in FIGS. 8a and 8b, two of the sidewalls 122 have a curved or concave upper surface 128. As discussed subsequently in FIGS. 11a-d, the curved upper surface 128 acts as a matched curved barrier for the coverglass thereby bumping against any clinging coverglasses.

Further, there is at least one cutout 116 along at least a portion of where the sidewalls 122 of the cartridge meet. In a preferred embodiment, as shown in FIG. 8a, the cutouts 116 are along the entire intersection where the sidewalls 122 meet (i.e., at each of the corners of interior 114. The cutouts may be of any shape. In one embodiment, the cutouts 116 are curved in shape. The cutouts 116 allow the edges of the coverglass to be protected from shattering. Typically, the edges of the coverglasses are prone to breakage. Because of the cutouts 116, the edges of the coverglasses to not touch the sidewalls 122, thereby reducing the possibility of cracking at the edges.

Figure 9A:
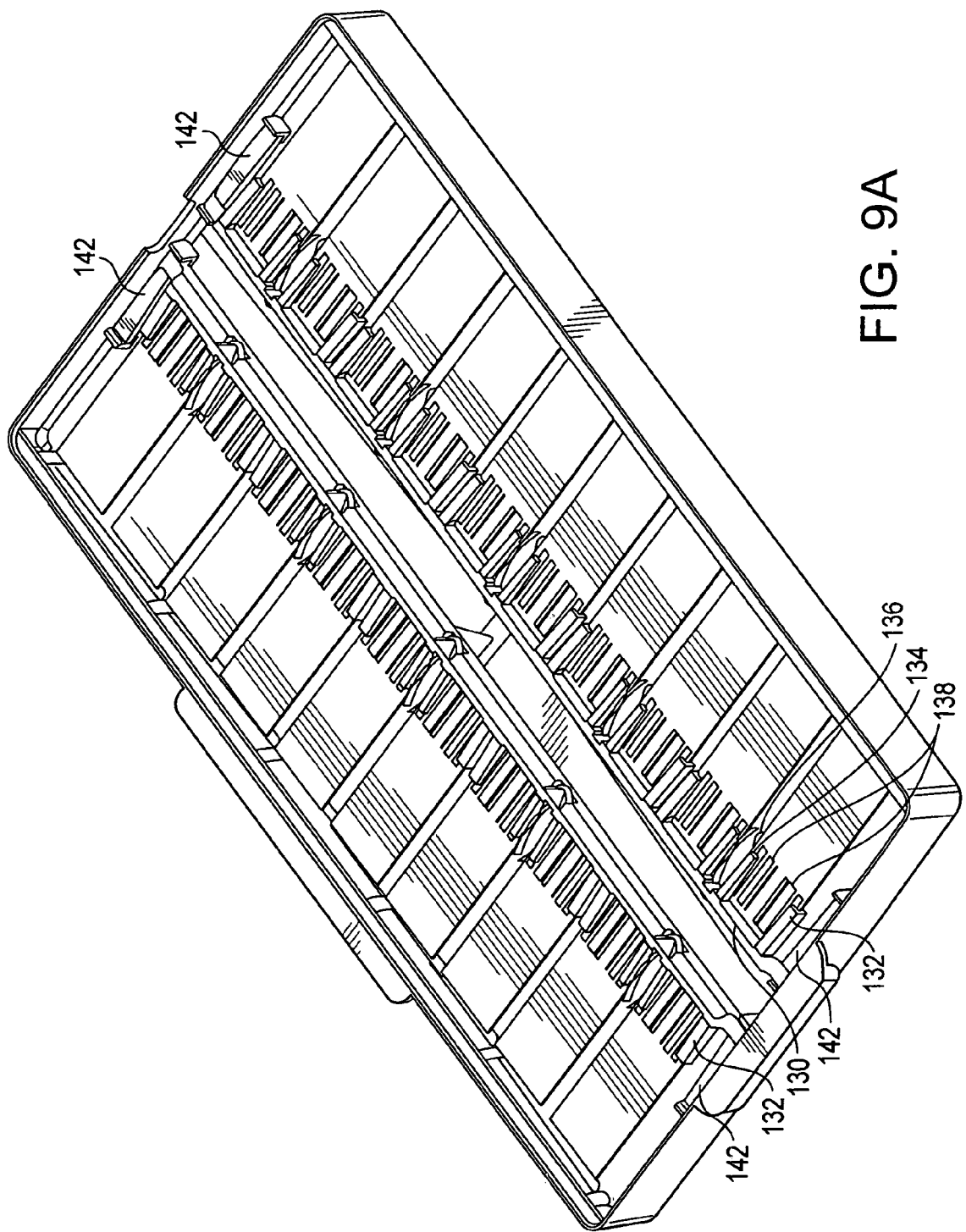
FIG. 9a is a top perspective view of a tray with vertebrae structure slide holders and slides.
Figure 9C:
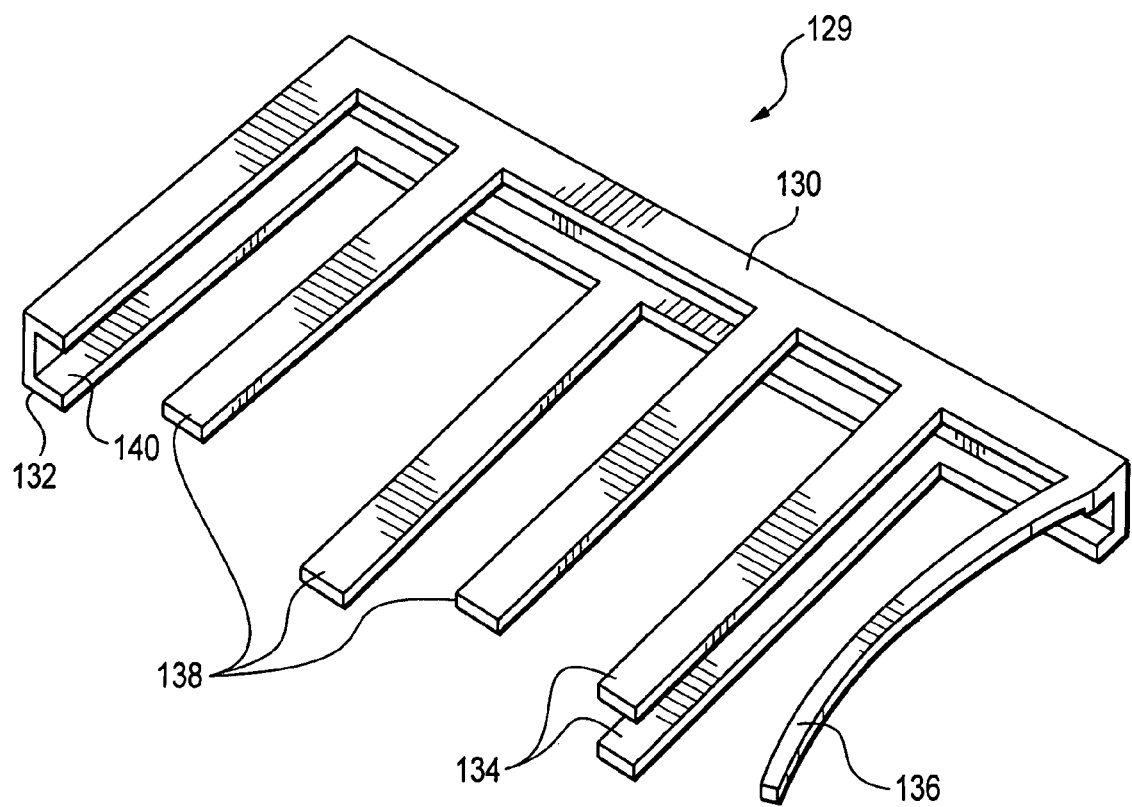
FIG. 9c is an individual section of the vertebrae structure slide holder.

Referring to FIG. 9a, there is shown a top perspective view of a tray with slide holders and slides. FIG. 9b is a partially exploded view of the tray in FIG. 9a. As shown in FIG. 9b, the slides are held in the tray 26 by a vertebrae structure 129. The vertebrae structure 129, in a preferred embodiment, have individual sections to hold each of the slides. In one embodiment, the individual section (shown in perspective view in FIG. 9c) of the vertebrae structure includes a main post 130, a stationary side post 132, a clip 134, a spring 136 and teeth 138. The stationary side post 132, clip 134, spring 136 and teeth 138 may be attached or integral with the main post. In one embodiment, some or all of the vertebrae structure 129 is manufactured by injection molding. Alternatively, some or all of the vertebrae structure 129 are composed of pieces connected or attached to the main post 130.

The clip 134 and the spring 136 work in conjunction to stabilize the slide and to seat an edge of the slide against the stationary post 132. Specifically, an edge of the slide (in a preferred embodiment, the longitudinal edge) is pushed by the spring so that an opposite edge is pushed against a surface 140 of the stationary post. The teeth 138 may be rectangular in cross section and may be placed such that, when the slide is inserted, at least one of the teeth abut a top surface of the slide and at least one of the teeth abut a bottom surface of the slide. Therefore, when the slide is inserted into the vertebrae structure, the slide is held securely.

The main post is placed inside tray 26. In one embodiment, the main post includes side arms 142 that engage feet 144, which may be attached to or integral with the tray. The side arms 142 are placed so that two edges of the side arms may be supported by the feet 144. The tray 26 further includes supports 146 which support a bottom side of the slide.

Figure 10A:
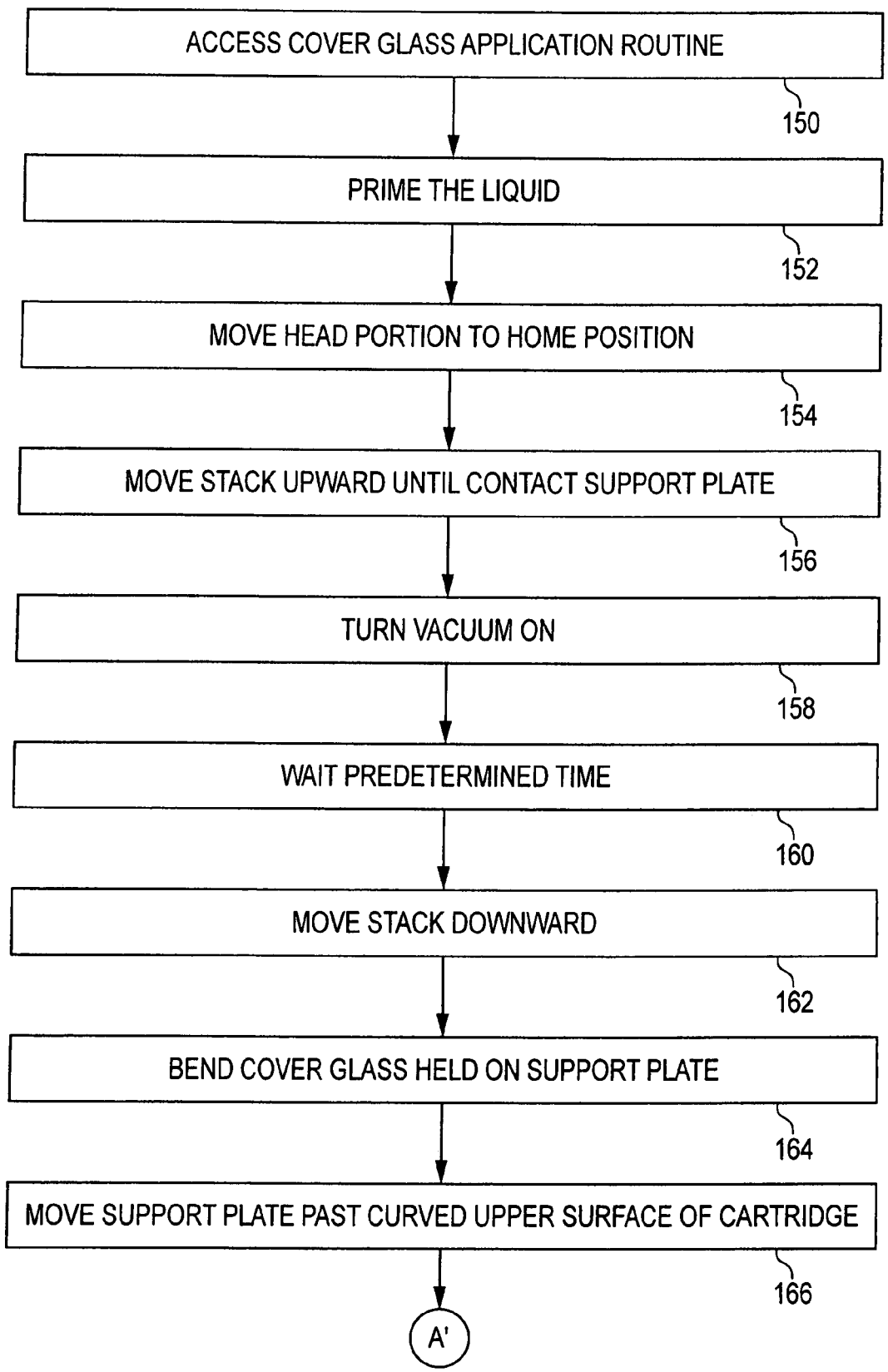
FIGS. 10a-10b are a flow chart of the steps of separating and dispensing a coverglass.
Figure 10B:
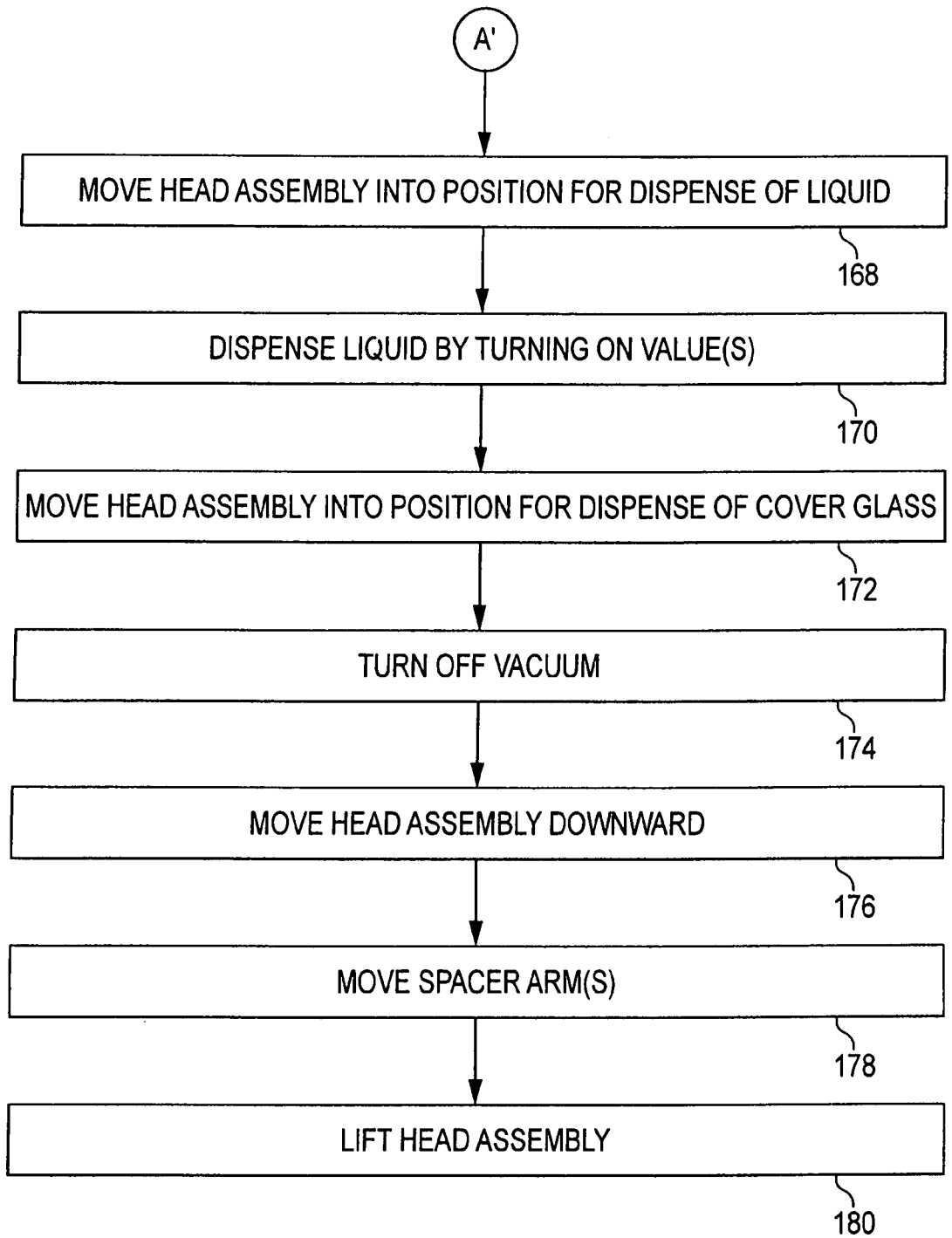

Referring to FIGS. 10a-10b, there is shown a flow chart of the steps of separating and dispensing a coverglass. The coverglass application routine is accessed, as shown at block 150. As discussed previously, the coverglass application routine may be accessed from memory 38 of the automated coverslipper module 18. The coverglass application routine may be placed in memory 38 either by downloading the routine from a host computer or by permanently (or semi-permanently) storing the routine in memory 38. The liquid for applying to the coverglasses is primed, as shown at block 152. In the embodiment where the head portion 20 includes dual head assemblies, there are liquid valves and associated tubing connecting the container of liquid to the nozzles 54 for each of the head assemblies. Priming of each of the head assemblies is performed separately by turning on the valve of the first head assembly and turning off the valve of the second head assembly being turned off, waiting a predetermined time, turning off the valve of the first head assembly and turning off the valve of the second head assembly being turned on, waiting a predetermined time, and turning off the valve of the second head assembly being turned off.

The head assembly is moved to the home position, as shown at block 154. Typically, motors 28 and 46 are used to move the head portion 20 to a predetermined position. In one embodiment, the head portion 20 is then moved from the home position to a position above cartridge 80 which contains the stack of coverglasses. In an alternative embodiment, the home position of the head assembly 20 is in a position above cartridge 80. The stack of coverglasses is then moved upward by motor 92 until contact with the flexible backing plate, as shown at block 158. The vacuum pump 43 is turned on, as shown at block 156. Processor 36 of the automated coverslipper module 18 may then wait a predetermined amount of time, as shown at block 160. The stack of coverglasses is then moved downward by motor 92, as shown at block 162. In one embodiment, the stack is moved downward approximately 1/10 of an inch. The flexible backing plate 64 is bent, thereby flexing the coverglass held by the flexible backing plate 64

(shown visually in FIG. 11b), as shown at block 164. The support block 50, while the flexible backing plate 64 is flexed, is then moved past curved upper surface 128 of cartridge 80 (shown visually in FIGS. 11c-d), as shown at block 166.

The coverglass is then dispensed onto the slide. As shown at block 168, the head assembly is moved into position for dispense of liquid. The liquid is then dispensed onto the slide, as shown at block 170. The head assembly is then moved into position for dispense of the coverglass attached to flexible backing plate 64, as shown at block 172. Alternatively, the position of the head assembly for dispensing of liquid and dispensing of the coverglass may be the same, obviating the need for moving the head assembly after the dispense of liquid. The vacuum pump 43 is turned off, as shown at block 174. This causes at least a portion of the coverglass to fall, by gravity, onto the slide. In one embodiment, one edge of the coverglass falls onto the slide (as shown in FIG. 12b). In a preferred embodiment, one of the longitudinal edges of the coverglass falls onto the slide. As shown at block 176, the head assembly is moved downward. In one embodiment, the head assembly is moved downward while only one edge of the coverglass touches the slide. In this manner, the edge opposite to the edge that touches the slide is moved proximate to the slide (e.g., between 60 to 100 thousandths of an inch from the surface of the slide) without touching the slide. This movement of the head assembly (and in turn the coverglass) downward may reduce the possibility of breakage of the coverglass and of trapping air bubbles underneath the coverglass. After the head assembly is moved downward, the spacer arm(s) may be moved, as shown at block 178. In this manner, the edge previously held by the spacer arm(s) is dropped onto the slide. In an alternative embodiment, after one edge of the coverglass is dropped onto the slide, the edge held by the spacer arm(s) may be dropped, bypassing the step of moving the head assembly downward. The head assembly is then moved upward, as shown at block 180

Referring to FIGS. 11a-d, there is shown a side view of one method of selecting a coverglass. In one embodiment, a stack 182 of coverglasses may be raised to the sealing member 72 by a motor 92. The motor 92 may run for a fixed period of time, thereby stalling when the stack 182 comes into contact with the support block 50. After the sealing member 72 couples with the top coverglass of the stack 182, the stack 182 may be lowered by the motor. To lower the stack 182, the motor 92 is run in reverse. In an alternate embodiment, the stack of coverglasses may remain stationary and the support block 50 is moved to contact the stack.

Figure 11A:
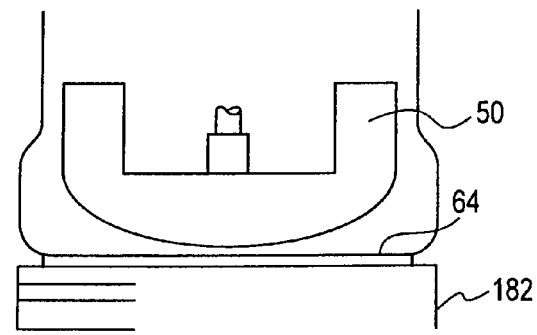
FIGS. 11a-11d show a method of separating coverglasses.

As shown in FIG. 11a, the coverglass is selected by suctioning it from the stack 182 of coverglasses. The top coverglass of stack 182 contacts sealing member 72. The coverglass preferably contacts at least a portion of sealing member 72, preferably over the entire sealing member 72. The seal may extend all the way to the perimeter of the coverglass. The supports 74 keep the sealing member 72 flat to reduce the possibility of concave cupping. Preferably, the suctioning mechanism (e.g., the vacuum pump) can be turned on after the sealing member 72 comes into contact with the stack 182. In an alternative embodiment, the suctioning mechanism can be turned on prior to contact with the stack 182. After contacting the sealing member 72, the spring member(s) 76 become compressed and store potential spring energy.

Figure 11B:
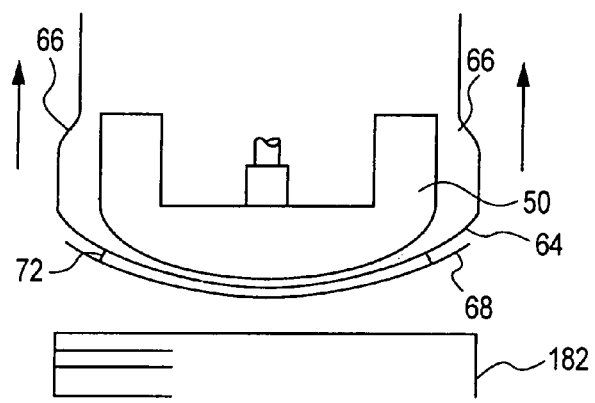

As shown in FIG. 11b, after selecting a coverglass 68, the flexible backing plate 64 and the sealing member 72 exert a force along one axis of the coverglass 68, and in one embodiment, the long axis of the coverglass 68 to slightly bend it at a constant radius to separate it from any clinging coverglasses 188 that may be sticking to the coverglass 68 selected. This is in contrast to prior art devices that exert a force on each end of the coverglass 68. This force is applied by raising the brackets 66 on each side of the support block 50. The brackets 66 and the flexible backing plate 64 move creating a flex bending action. The flex bending action causes the top coverglass to peel away from other coverglasses in the stack. Since the seal may extend to the outer perimeter of the coverglass, a greater bending may be achieved at the outer edges of the coverglass during separation without overstressing the material. This is in contrast to certain devices in the prior art which use suction mechanisms to apply a great amount of bending moment in the middle of the coverglass (and a lesser amount of force on the edges of the coverglass).

The coverglass 68 may take on a smooth curved shape due to the equal (or near equal) bending action taking place. The coverglass 68 will receive an equal amount of stress applied over the entire area of the coverglass 68 because of the seal formed between the sealing member 72 and the coverglass 68. Bending the top glass on the stack 182 to separate it from the stack 182 is a reliable method of separating the coverglasses. Another embodiment may have the flexible backing plate 64 using a twisting action to instigate the release of sticking coverglasses. Any method of temporarily reshaping the coverglass 68 will assist in the separation process.

Figure 11C:
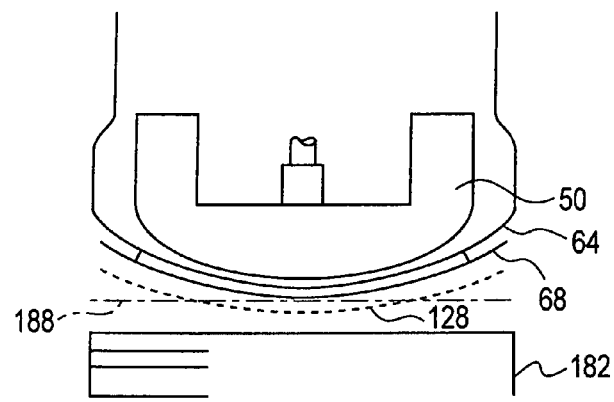
Figure 11D:
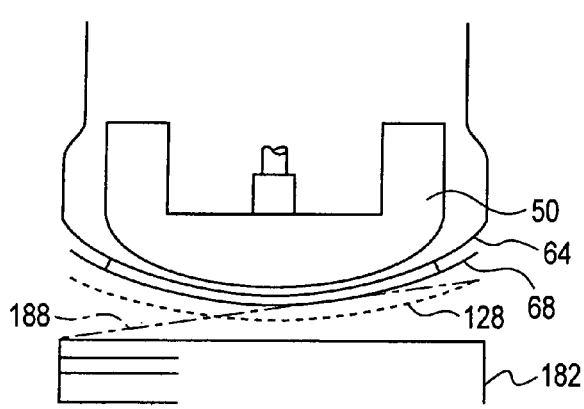

To further increase the chances of a reliable separation, the bent coverglass is passed through curved upper surface 128 (also shown in FIGS. 8a and 8b). The curved upper surface 128 acts as a matched (or near-matched) curved barrier for the coverglass thereby bumping against any clinging coverglasses 188. As shown in FIGS. 11c and 11d, the curved upper surface 128 used to wipe underneath the support block 50 is preferably matched to the shape of the bent or twisted coverglass. Another embodiment may have the curved upper surface 128 pass underneath the fixed support block 50. FIG. 11c shows a first orientation for a clinging coverglass 188 to stick onto the selected coverglass 68. FIG. 11d shows a second orientation for a clinging coverglass 188 to stick onto the selected coverglass 68. The matched curved barrier, represented by the side profile of the curved upper surface 128 in the figures, would reject these clinging coverglasses 188 as shown in FIGS. 11c and 11d, when the sealing member assembly is rotated away from the stack 182. This wiping action removes any clinging coverglasses 188, and places those coverglasses clinging to the selected coverglass back onto the remaining stack 182 for future selection.

A side profile of the curved upper surface 128 which is shown in FIG. 11c and FIG. 11d may take on a different shape so as to match the shape of the temporarily reshaped coverglass 68. The selected coverglass is passed close enough to the curved upper surface 128 to remove any clinging coverglasses 188. Another embodiment may have the wiping action taking place underneath the support block 50 with a motor driven device matching the shape of the temporarily reshaped coverglass.

Figure 12A:
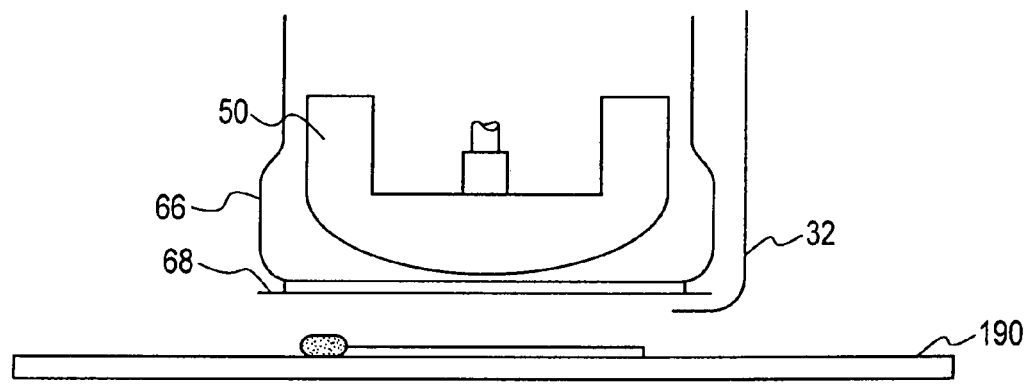
FIGS. 12a-12c show schematics depicting a method of dispensing a coverglass onto a slide.
Figure 12B:
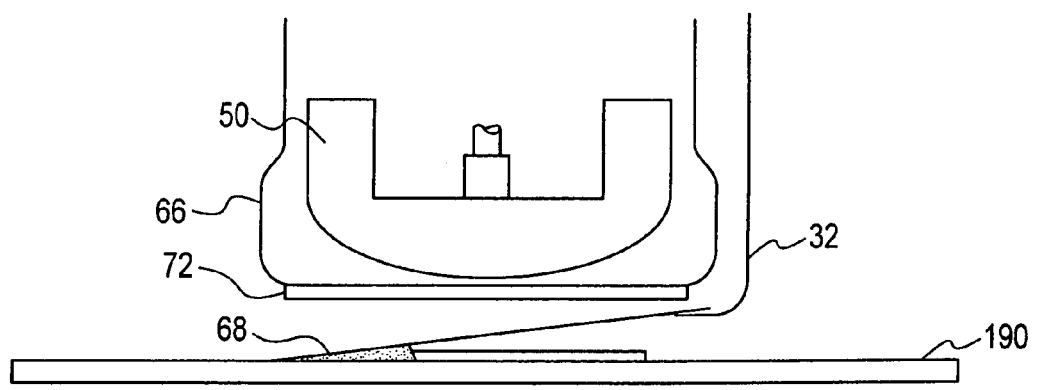
Figure 12C:
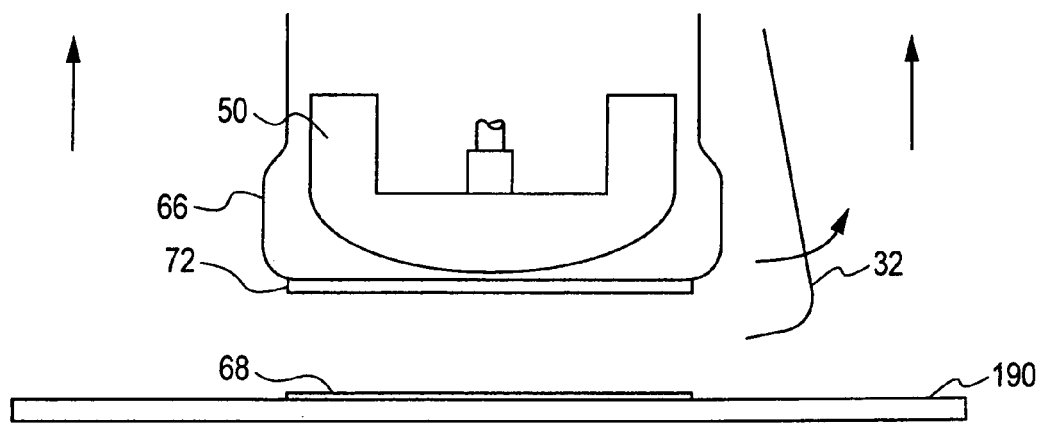

Referring to FIG. 12a-c, there is shown a side view of a method of releasing the coverglass onto a slide. In one aspect, bonding fluid is placed on one portion of the slide by bonding fluid nozzles 54, as shown in FIG. 3. As previously mentioned, the bonding fluid may be a glue solvent, in a preferred embodiment, or glue. Pre-glued coverslips are disclosed in co-pending application Ser. No. 09/716,344 (Crouch et al., incorporated herein by reference in its entirety. A first edge of the coverglass is released onto the portion of the slide where the bonding fluid is placed so that the coverglass forms a "V" shape relative to the slide (see FIG. 12b). Thereafter, a second edge, opposite the first, of the coverglass is released (or forced downward) to cover the slide (see FIG. 12c). In this manner, one can minimize the number of gas bubbles trapped underneath the coverglass.

Initially, the specimen is prepared by applying bonding fluid onto the slide. The bonding fluid is preferably applied on the surface of the slide at or near one of the longitudinal edges of the slide. In one embodiment, four or five discrete drops of bonding fluid may be applied. Alternatively, a bead of bonding fluid along the longitudinal edge may be applied. The placement of the coverglass in the relative position to the slide may be accomplished by moving either the support block 50, moving the slide 190, or a combination of both. In a preferred embodiment, the slide 190 remains stationary. The coverglass is then dropped onto the slide, with one of the coverglass's edges touching the slide. This may be performed by turning off the vacuum pump and allowing gravity to carry an edge of the coverglass onto the slide. In a preferred embodiment, the longitudinal edge of the coverglass is dropped onto the slide. In one embodiment, an external device, such as a hook (see e.g., spacer arm 32 in FIG. 3), may be used to drop one edge of the coverglass onto the slide. In an alternative embodiment, the support block 50 may be pivoted so that, while the coverglass is still being held by the support block 50, an edge of the coverglass 68 may be lowered to the slide 190.

FIG. 12a shows the support block 50 with a coverglass 68 in the dispensing position. A spacer arm 32 is placed between one edge of the coverglass 68 and the slide 190. The spacer arm 32 may be pivotally attached to the sealing member assembly so that it pivots away from the assembly when it is in a down position. The spacer arm 32 acts as a hook which catches one end of the coverglass 68 as the vacuum is removed. The spacer arm 32 is a bar, preferably of metal, which is less than 0.25" wide. In a preferred embodiment, the spacer arm 32 may be pivotally connected to the sealing member assembly. After placement of the spacer arm 32, the suctioning mechanism is turned off allowing the coverglass 68 to fall freely via gravity as mentioned earlier, and with the force exerted by the spring member(s) 76, the coverglass 68 may be pushed away from the sealing member assembly.

One embodiment of the mounting of the spring member(s) 76 is to place one near each corner of the flexible backing plate 64 within the perimeter of the sealing member 72 as shown in FIG. 5. Alternatively, the spring member(s) 76 may be placed outside of the perimeter of the sealing member 72. The preferred embodiment comprises four spring members 76, one spring member 76 placed near each corner of the sealing member 72, but alternative embodiments may contain more or fewer spring members 76. The spring member(s) 76 are compressed when the coverglass 68 is suctioned to the sealing member 72. Upon release of the coverglass 68 via turning off the vacuum generator, the spring member(s) 76 exert a restoring force to the coverglass 68 pushing it away from the sealing member 72 and allowing it to fall or be drawn onto the slide 190. This insures the disengagement of the coverglass 68 from the sealing member 72.

The spring member(s) 76 may be of a conical, or spherical shape and comprise a resilient elastomeric material. In the preferred embodiment, four spring members 76 of a conical shape are placed at the corners of the sealing member 72. All four spring members 76 exert a force onto the coverglass 68, due to the buildup of potential spring energy, at or near the same instant of time. The conical spring member(s) 76 preferably take on a cone shape, positioned so that the tip of the cone contacts the coverglass 68, and the base of the cone is mounted inside the perimeter of the sealing member 72 on the underside of the flexible backing plate 64. Using the tip of the cone to contact the coverglass 68 lowers the surface area between the cone spring member(s) 76 and the coverglass 68 that will come into contact. This lowers the possibility of the coverglass 68 sticking to the cones. Preferably, they are welded onto sealing member 72.

In reference to FIG. 12b, when the coverglass 68 is released from the sealing member 72, at least one edge of the coverglass 68 will fall and contact at least one edge of the slide 190, and the other edge of the coverglass 68 will fall and contact the spacer arm 32. This creates a wedge-shaped gap between the slide 190 and the coverglass 68.

As discussed previously, liquid is placed on one portion of the slide so that the liquid is in the notch or apex of the "V" shape formed by the coverglass 68 and the slide 190, as shown in FIG. 12b. Either the longer or shorter edge of the rectangular shaped coverglass 68 may contact the slide 190. As discussed in the background of the invention, coverglasses are typically 1" by 2". In a preferred embodiment, the longer edge (2") of the coverglass is in contact with the slide. Alternatively, contacting the coverglass 68 with the slide 190 may be accomplished by tilting the support block 50 relative to the slide 190. In this embodiment, no spacer arm 32 would be needed. Furthermore, in this embodiment, when the coverglass 68 is released from the sealing member 72, one edge will contact the slide 190 first, creating the wedge shaped gap discussed earlier. Another embodiment may have the slide 190 tilted with respect to the support block 50. Again, in this embodiment, after the coverglass 68 is released from the sealing member 72, one edge of it will contact the slide 190 first, creating the desired wedge-shaped gap between the two.

Once the coverglass 68 contacts the slide 190, the head assembly may be moved downward. In one aspect, the head assembly is moved downward so that the edge, which is opposite to the edge which first touched the slide, is close, but not touching the slide (e.g., 60-100 thousands of an inch). Thereafter, the spacer arm 32 may be removed and the support block 50 is raised allowing the opposite edge of the coverglass 68 to fall completely onto the slide 190. This is shown in FIG. 12c. In a preferred embodiment, the spacer arm 32 is removed by either swinging it away from the support block 50, or pivoting it away. Another embodiment may have the spacer arm 32 rotate at least 90° to allow the coverglass 68 to fall onto the slide 190. In an alternate embodiment, the spacer arm 32 remains stationary while the slide 190 is lowered relative to the support block 50 a distance great enough for the coverglass 68 to fall off of the spacer arm 32 and onto the slide 190. When the spacer arm 32 is removed, allowing the coverglass 68 to fall freely, the coverglass 68 will not be dragged by the spacer arm 32 off of the slide 190 because the bonding fluid on the specimen has a retaining force holding the coverglass 68 in place. In still an alternate embodiment, a mechanical stop may be placed such that, when the spacer arm 32 is removed, the coverglass 68 may hit the mechanical stop if the coverglass 68 adheres to spacer arm.

After the first edge of the coverglass 68 has initially contacted the specimen and bonding fluid on the slide 190, capillary action will pull bonding fluid to the sharp corner of the wedge gap between the coverglass 68 and the slide 190. The initial three or four discrete drops of bonding fluid will form a continuous bead with no gaps between them. The bonding fluid will act to draw the coverglass and the slide together. As the head assembly is moved downward and/or as the released coverglass tilts down onto the specimen, the advancing bonding fluid line pushes air out from underneath the coverglass 68 as the coverglass 68 lowers. The movement of the bonding fluid within the spaces between the coverglass 68 and the slide 190 may take place due to the forces of capillary action. The final result is the placement of the coverglass 68 completely covering the specimen on the slide 190 with little or no trapped air pockets.

An exemplary embodiment of the present invention has been illustrated and described. It will be understood, however, that changes and modifications may be made to the invention without deviating from the scope of the invention, as defined by the following claims. Further, the claims should not be read as limited to the described order of elements unless stated to that effect. Therefore, all embodiments that come within the scope and spirit of the following claims and equivalents thereto are claimed as the invention.

We claim:

1. A method for automatically removing a coverglass from the top of a stack of coverglasses contained within a cartridge, the coverglass having edges, the method comprising the steps of:
    forming a seal proximate to the edges of the coverglass;
    exerting a force along the proximate seal, uniformly bending the coverglass along a longitudinal axis to separate the coverglass from the stack of coverglasses; and
    moving the bent coverglass away from the cartridge, wherein the cartridge has an upper surface, and the moving of the coverglass away from the cartridge causes any un-separated coverglasses to be dislodged from the bent coverglass by the cartridge upper surface; wherein the step of forming a seal includes contacting the coverglass with a sealing member, the sealing member being attached to or integral with a flexible backing plate and being composed of an elastomeric material.

2. The method of claim 1, wherein the step of forming a seal includes contacting the coverglass with a sealing member, the sealing member consisting of a single sealing member that forms a seal along a circumference of the coverglass.

3. The method of claim 1, wherein the flexible backing plate includes a conduit connected to a vacuum source and wherein the step of forming a seal further includes applying vacuum to the sealing member.

4. The method of claim 3, wherein the step of applying the vacuum is performed after the step of contacting the coverglass with the sealing member.

5. The method of claim 1, wherein the step of uniformly bending the coverglass includes bending the coverglass at about a constant bend radius.

6. The method of claim 5, wherein the step of bending the coverglass further includes bending the coverglass along a long axis such that the distal ends of the long axis of the coverglass approach each other.

7. The method of claim 1, further comprising the step of moving the stack of coverglasses and the removed coverglass relative to one another.

8. The method of claim 7, wherein the stack of coverglass is moved within a cartridge, the cartridge comprising one or more apertures in the bottom end of the cartridge for allowing entry of a fork to move the stack of coverglasses.

9. The method of claim 1, further comprising automatically dispensing the coverglass onto a slide.

10. The method of claim 9, wherein dispensing comprises the steps of:
    releasing a first edge of the coverglass to touch a portion of the slide; and
    releasing a second edge of the coverglass onto the slide, the second edge being opposite to the first edge of the coverglass.

11. The method of claim 10, wherein the step of releasing a first edge of the coverglass to touch a portion of the slide comprises positioning the coverglass so that the coverglass and the slide form a "V" shape.

12. The method of claim 10 further comprising the step of dispensing liquid onto the slide, the step of dispensing liquid being performed prior to the step of releasing the first edge of the coverglass to touch a portion of the slide.

13. The method of claim 12, wherein the first edge of the coverglass and the slide intersect to form a line, and wherein the liquid is dispensed proximate to the line.

14. The method of claim 10, wherein the coverglass comprises a rectangular shape with a 2 shorter sides and 2 longer sides, and wherein the first edge is one of the 2 longer sides.

15. The method of claim 10, wherein the coverglass is uniformly bent around the support block by suction, and wherein the step of releasing the first edge onto the slide comprises removing the suction so that the first edge of the coverglass drops onto the slide by gravity.

16. The method of claim 15, wherein the support block includes a spacer arm, and wherein the second edge of the coverglass is held by the spacer arm after removing the suction.

17. The method of claim 16, wherein the step of releasing the second edge of the coverglass onto the slide comprises moving the spacer arm so that the second edge of the coverglass drops onto the slide by gravity.

18. The method of claim 10, wherein after the step of releasing the first edge of the coverglass to touch a portion of the slide, the coverglass and slide form a first angle, the first angle being less than 90 degrees, and further comprising the step of moving the support block and slide relative to one another so that the coverglass and slide form a second angle, the second angle being less than the first angle, wherein the step of moving the support block and slide relative to one another is performed after the step of releasing the first edge of the coverglass but before the step of releasing the second edge of the coverglass.

19. The method of claim 18, wherein the step of moving the support block and slide relative to one another comprises moving the support block downward.

* * * * *

UNITED STATES PATENT AND TRADEMARK OFFICE
CERTIFICATE OF CORRECTION

PATENT NO. : 7,727,774 B2 Page 1 of 1
APPLICATION NO. : 11/838104
DATED : June 1, 2010
INVENTOR(S) : Kurt Reinhardt, Anthony Ford and Mirek Holubec It is certified that error appears in the above-identified patent and that said Letters Patent is hereby corrected as shown below:

In claim 15, at column 16, line 27, delete "the" and insert --a-- so that line 27 reads as follows:

uniformly bent around a support block by suction, and

Signed and Sealed this

Seventh Day of December, 2010

David J. Kappos
*Director of the United States Patent and Trademark Office*